United States Patent [19]

Chan et al.

[11] Patent Number: 5,301,693
[45] Date of Patent: Apr. 12, 1994

[54] SMOKING COMPOSITIONS CONTAINING AN α-ALKYLCINNAMALDEHYDE-RELEASE ADDITIVE

[75] Inventors: W. Geoffrey Chan, Chesterfield; William B. Edwards, III, Richmond; Harvey J. Grubbs, Mechanicsville; Yoram Houminer; Charles R. Howe, both of Richmond; John D. Naworal, Midlothian; John B. Paine, III, Richmond; Kenneth F. Podraza, Richmond; Edward B. Sanders, Richmond; Jeffrey I. Seeman, Richmond; Everett W. Southwick, Richmond, all of Va.

[73] Assignees: Philip Morris Incorporated, New York, N.Y.; Philip Morris Products Inc., Richmond, Va.

[21] Appl. No.: 911,274

[22] Filed: Jul. 9, 1992

[51] Int. Cl.$^5$ .................. A24B 15/30; C07C 57/03
[52] U.S. Cl. ........................ 131/276; 554/219; 562/470; 426/538; 426/533
[58] Field of Search ............ 131/276; 554/219; 562/470; 426/533, 538

[56] References Cited

U.S. PATENT DOCUMENTS 4,036,237  7/1977  Teng .................................. 131/17

OTHER PUBLICATIONS

CA81: 104640; Bensimon; 1974.

*Primary Examiner*—José G. Dees
*Assistant Examiner*—Samuel Barts
*Attorney, Agent, or Firm*—James E. Schardt

[57] ABSTRACT

This invention provides smoking compositions which contain a novel β-hydroxycarboxylate flavorant-release additive. Under cigarette smoking conditions, a combustible filler and/or paper wrapper additive such as calcium bis(2,2-diethyl-3-hydroxy-4-phenylmethylenedecanoate) pyrolyzes and releases α-hexylcinnamaldehyde as a volatile flavorant component of the cigarette smoke.

32 Claims, No Drawings

SMOKING COMPOSITIONS CONTAINING AN α-ALKYLCINNAMALDEHYDE-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 3,379,754; and the like.

J. C. Leffingwell et al "Tobacco Flavoring For Smoking Products" (R. J. Reynolds Publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as l-menthyl linalool carbonate. Under smoking conditions pyrolysis of the carbonate ester releases menthol which flavors the mainstream smoke.

U.S. Pat. No. 3,332,428 and U.S. Pat. No. 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,117,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

Of specific interest with respect to the present invention is the proposed utilization of an organic additive to a cigarette paper wrapper to modify sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethylvanillyl-D-glucoside yields ethylvanillin and levoglucosan as pyrolysis products.

There is continuing research effort to develop low delivery smoking compositions which generate mainstream smoke with enhanced taste and sidestream smoke with a palliated aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel β-hydroxycarboxylic acids and β-hydroxycarboxylate salts which are adapted to be incorporated into cigarette filler and/or paper wrapper components, and which under normal smoking conditions release α-hexylcinnamaldehyde as a volatile flavorant compound of the cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.000–5 weight percent, based on the total weight of filler, of a flavorant-release additive corresponding to the formula:

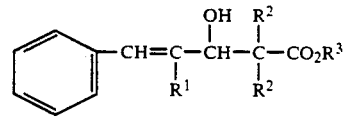

where $R^1$ is a $C_4$–$C_7$ alkyl substituent, $R^2$ is a $C_1$–$C_4$ alkyl substituent, and $R^3$ is hydrogen or an alkali metal or alkaline earth metal atom.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

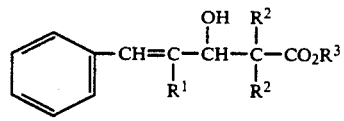

where $R^1$ is a $C_4$–$C_7$ alkyl substituent, $R^2$ is a $C_1$–$C_4$ alkyl substituent, and $R^3$ is hydrogen or an alkali metal or alkaline earth metal atom.

A cigarette smoking product in accordance with the present invention typically contains between about 0.01–5 weight percent of flavorant-release additive in the paper wrapper. The additive can be present as a surface coating or absorbed component of the paper wrapper, and/or the additive can be incorporated as a component of the adhesive formulation which is utilized to seal the sideseam of cigarette paper wrappers.

In a further embodiment an invention cigarette product contains between about 0.01–5 weight percent of flavorant-release additive in the paper wrapper, and contains between about 0.0001–5 weight percent of flavorant-release additive in the combustible filler, based on the weight of filler.

A present invention flavorant-release additive which is incorporated in smoking compositions as described above is a low volatility compound which under normal smoking conditions pyrolyzes into volatile constituents, one of which is α-hexylcinnamaldehyde which enhances the flavor and aroma of low delivery cigarette smoke:

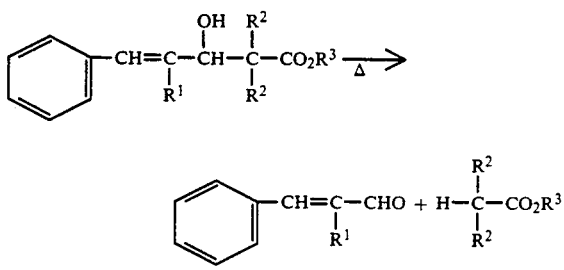

$R^1$ in the formula is a $C_4$–$C_7$ alkyl substituent such as n-butyl, 2-butyl, isobutyl, n-pentyl, n-hexyl, 2-hexyl, isohexyl and n-heptyl.

$R^2$ in the formula is a $C_1$–$C_4$ alkyl substituent such as methyl, ethyl, n-propyl, isopropyl, n-butyl, 2-butyl, and isobutyl.

Preparation Of Flavorant-release Compounds

One method of preparing the β-hydroxycarboxylate flavorant-release compounds is by the reaction of an enolate disalt of dialkylacetic acid with α-alkylcinnamaldehyde:

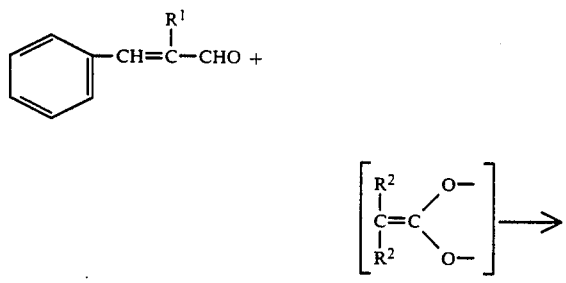

The reaction is conducted in the presence of a strong base such as lithium diisopropylamide alone or in combination with an alkali metal hydride. The strong base initiates the in situ formation of the dianion intermediate reactant.

Typically the strong base is added to the carboxylate starting material in an inert solvent medium such as tetrahydrofuran or heptane maintained at a temperature between about −80° C. and 50° C. and under an inert atmosphere.

In a subsequent step the α-alkyloinnamaldehyde reactant is added to the reaction medium at a temperature between about −80° C. and 25° C.

The resultant β-hydroxycarboxylate type of addition products are white solids when in the form of salts. A salt is provided by reacting the acid form with an appropriate base. The $R^3$ cation substituent as represented in the herein described structural formula can be lithium, sodium, potassium, calcium or magnesium.

Preparation Of Tobacco Compositions

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to the formula:

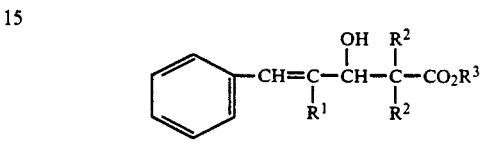

where $R^1$ is a $C_4$–$C_7$ alkyl substituent, $R^2$ is a $C_1$–$C_4$ alkyl substituent, and $R^3$ is hydrogen or an alkali metal or alkaline earth metal atom.

The invention β-hydroxycarboxylate flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously described hereinabove, an invention flavorant-release additive also can be incorporated in the paper wrapper of cigarette products, for the purpose of modifying the aroma of cigarette sidestream smoke under smoking conditions. The additive can be applied to the paper wrapper in the form of a solution, or a suspension of fine particles. Alternatively, the additive can be included as an ingredient during the cigarette paper making process.

A further method of incorporating a flavorant-release additive in a cigarette smoking composition is by including the additive as an ingredient in the paper wrapper sideseam adhesive formulation which is employed in cigarette fabrication.

A present invention flavorant-release compound has unique properties when incorporated into cigarette filler and/or paper wrapper matrices. Under normal smoking conditions α-alkylcinnamaldehyde is smoothly and efficiently released as a volatile flavorant component of the cigarette smoke. The α-alkylcinnamaldehyde palliates the harshness and irritation of sidestream smoke.

The following Examples are further illustrative of the present invention. The specific ingredients and processing parameters are presented as being typical, and various modifications can be derived in view of the foregoing disclosure within the scope of the invention.

EXAMPLE I

3-Hydroxy-2,2-dimethyl-4-phenylmethylenedecanoic acid

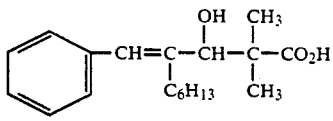

A 3-necked flask was charged with 7.75 g (0.075 mole) of diisopropylamine, 3.7 g (0.085 mole) of sodium hydride (60% in mineral oil) and 75 mL of tetrahydrofuran. A 6.6 g (0.075 mole) quantity of isobutyric acid was added to the stirred mixture. The internal temperature rose to 55° C., and the hydrogen evolution was completed by heating the mixture to reflux for 15 minutes.

The reaction medium was cooled to 0° C. and 47 mL of 1.6 Molar n-butyllithium was added, while maintaining the temperature below 10° C. After addition was completed, the mixture was warmed to room temperature, and allowed to stand at 50° C. for 30 minutes. The reaction medium was cooled to 0° C. and α-hexylcinnamaldehyde (14 g, 0.065 mole) was added dropwise over a 15 minute period. The solution then was stirred at room temperature for 2 hours.

A 100 g quantity of ice was added to the reaction mixture, and the organic layer was separated. The organic layer was washed with 50 mL of water, and the combined aqueous layer was washed with 2×50 mL of diethyl ether. Water (25 mL) was added to the combined diethyl ether solution, and the mixture was acidified to pH 2 with dilute hydrochloric acid. The ether layer was separated, and the aqueous layer was washed with 2×25 mL of diethyl ether. The combined ether solution was dried with anhydrous magnesium sulfate, and after filtration of solids and evaporation of the filtrate under rotary evaporation, 12 g of light yellow oil was obtained. The oil was dissolved in hexane and upon standing the desired product crystallized out of solution. Yield 8.0 g (41%). NMR and IR confirmed the title structure.

Anal. calc. for $C_{19}H_{28}O_3$: C,74.96; H,9.27
Found: C,74.75; H,9.22

A similar procedure is employed to produce related organic acids by utilizing α-butylcinnamaldehyde, α-pentylcinnamaldehyde or α-hexylcinnamaldehyde in place of α-hexylcinnamaldehyde.

EXAMPLE II

Calcium bis(3-hydroxy-2,2-dimethyl-4-phenylmethylenedecanoate)

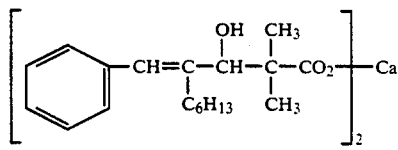

A 1 g (0.018 mole) quantity of calcium oxide was suspended in 100 mL of distilled water, and 4 g (0.013 mole) of 4-hexyl-3-hydroxy-2,2-dimethyl-5-phenyl-4-pentenoic acid was added to the suspension. After stirring for 4 days at room temperature, 50 mL of dichloromethane was added to the suspension and the mixture was stirred vigorously for 30 minutes. Another 50 mL of dichloromethane was added and the aqueous layer was separated. The aqueous phase was washed with 50 mL of dichloromethane, and the combined organic phase was evaporated to dryness to provide 4.8 g of crude product.

The product was dissolved in hexane, and the solution was filtered, and the solvent was removed by rotary evaporation. The residual solid was dissolved in acetone, and the solvent was evaporated under a stream of nitrogen to yield 4.2 g (95%) of product. NMR and IR confirmed the title structure.

EXAMPLE III 2,2-Diethyl-3-hydroxy-4-phenylmethylenedecanoic acid

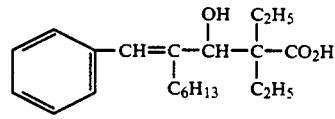

Method A

Sodium hydride (81.7 g, 60%, 2.042 moles) and n-hexane (500 mL) were added to tetrahydrofuran (1000 mL) in a reactor. 2-Ethylbutyric acid (232.4 g, 2.00 moles) was added in portions over a 35 minute period, and the resulting clear solution was further diluted with tetrahydrofuran (1000 mL).

Diisopropylamine (209.3 g, 2.068 moles) was added, and the reaction medium cooled (ice bath). n-Butyllithium (800 mL, 2.5 Molar in hexane, 2.00 moles) was added via cannula over 63 minutes at a temperature in the range of 12°–18° C. The reaction medium was heated with stirring and maintained at about 50° C. for 1 hour. The reaction medium was cooled (ice bath), and then with stirring α-hexylcinnamaldehyde (432.9 g, 2.001 moles) was added over 52 minutes, with the temperature at 20° C. or below. The resulting product mixture under nitrogen was allowed to warm to room temperature and stand for about 18 hours.

The product mixture was extracted with water (2000 mL), and the aqueous phase was discarded. The reacting organic phase was extracted with a second portion of water (2000 mL) to obtain the product in the aqueous phase. The aqueous phase was acidified (conc. HCl, 200 mL) and extracted with hexane (1000 mL). The organic phase was isolated, filtered, and concentrated in vacuo to provide the crude product as a viscous oil (552.9 g).

The crude product was purified on a small scale by gel permeation/size exclusion high pressure liquid chromatography, and on a larger scale by flash chromatography over silica gel, using ethyl acetate/n-hexane. Carbon-13 and NMR confirmed the title structure.

Anal. calc. for $C_{21}H_{32}O_3$: C,75.86; H,9.70
Found C,76.07; H,10.08

Method B

To a cooled solution of 10.1 g (0.10 mole) diisopropylamine in 50 mL of heptane was added dropwise 5.8 g (0.05 mole) of diethylacetic acid, and a translucent white solid suspension formed. With continued cooling, 40 mL of 2.5M n-butyllithium in hexane was added dropwise to the reaction medium. After the addition was completed, the reaction medium was heated at 80° C. for one hour.

The resulting reaction mixture was cooled in the ice bath and treated dropwise with 10.8 g (0.05 mole) of α-hexylcinnamaldehyde. The reaction mixture was stirred for one hour at room temperature, and then hydrolyzed with excess dilute hydrochloric acid.

The organic phase was separated, washed twice with 75 mL of water, dried over sodium sulfate, and concentrated on a rotary evaporator to yield 16.3 g of a viscous yellow oil.

EXAMPLE IV

Calcium bis(2,2-diethyl-3-hydroxy-4-phenylmethylenedecanoate

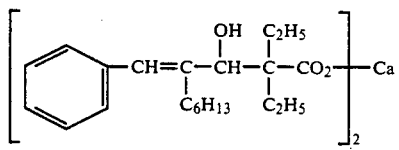

Method A

Calcium oxide was freshly prepared by ignition of calcium carbonate (ACS reagent grade) in a porcelain crucible at 950°–1000° C. for about six hours.

The decanoic acid of Example III, Method A, (29.5 g, 0.089 mole, purified by flash chromatography) was dissolved with warming in n-hexane (500 mL), and water (250 mL) was added. Calcium oxide (2.5 g, 0.046 mole) was slaked in water (200 mL), and added to the reaction medium with vigorous agitation. A solid product crystallized from the hexane phase. The product medium was suction filtered, and the white filtercake was rinsed with water (100 mL), n-hexane (100 mL), and then dried. A yield of 28.7 g (90%) was obtained. Carbon-13 and NMR confirmed the title structure.

Anal. calc. for $C_{42}H_{62}CaO_6$: C,71.76; H,8.89; Ca,5.70
Anal calc. for $C_{42}H_{62}CaO_6H_2O$: C,69.96; H,8.95; C,5.56
Found C,69.80; H,8.98; Ca,5.76
TGA analysis suggests a monohydrate compound.

Method B

1. Synthesis in n-hexane.

The decanoic acid of Example III, Method A, (266.4 g) was dissolved in n-hexane (500 mL). Calcium oxide (20.4 g, 0.365 mole) was slaked in water (1000 mL). n-Hexane (1000 mL) was layered on top of the calcium oxide slurry, and the decanoic acid solution was added with vigorous agitation. After several hours of standing, a crystalline solid separated from solution. The solid was filtered, washed thoroughly with n-hexane, and dried in air. A 234.3 g (89%) yield of product was obtained. NMR indicated that the product was a pure single isomer calcium salt.

2. Synthesis in dry n-heptane.

The decanoic acid of Example III, Method A, (164.0 g) in heptane was added to dry calcium hydroxide (16.6 g, 0.225 mole). The admixture was stirred vigorously, and the calcium hydroxide dissolved almost completely. On standing overnight, a crystalline solid formed in the organic phase. The solid was recovered by filtration, washed with heptane (1000 mL) and dried in air. A yield of 164.2 g (90%) was obtained. NMR spectra indicated that this product was a pure single isomer calcium salt.

EXAMPLE V

3-Hydroxy-2-methyl-2-propyl-4-phenylmethylenedecanoic acid

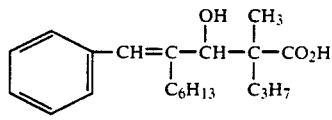

The reaction of 5.8 g (0.05 mole) 2-methylvaleric acid with 10.8 (0.05 mole) of α-hexylcinnamaldehyde was conducted in the manner described in Example III, Method B. The product was isolated as a viscous yellow oil. NMR spectra confirmed the title structure.

EXAMPLE VI

Calcium bis(3-hydroxy-2-methyl-2-propyl-4-phenylmethylenedecanoate

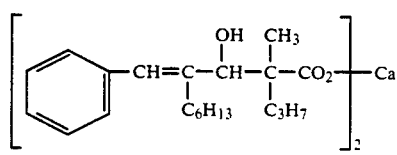

The compound of Example V was converted to its Ca-salt by the procedure described in Example IV, Method B2, except that calcium hydroxide was used instead of calcium oxide. The product was isolated as a white solid. NMR spectra confirmed the title structure.

EXAMPLE VII

A 2% solution in 95% ethanol of the invention Alpha-hexylcinnamaldehyde-release additive described in Example IV was applied to the paper wrapper of cigarettes (about 0.3 mg per cigarette) and the cigarettes were smoked and evaluated by an experienced smoking panel. Compared to untreated control cigarettes, the treated cigarettes exhibit pleasant floral-green, herbal-spicy aromas in the sidestream smoke, without a significant change in the mainstream smoke flavor. The sidestream smoke was also reported to be less irritating compared to the control.

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

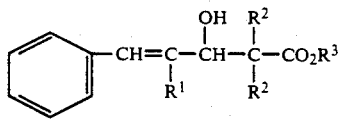

where $R^1$ is a $C_4$-$C_7$ alkyl substituent, $R^2$ is a $C_1$-$C_4$ alkyl substituent, and $R^3$ is hydrogen or an alkali metal or alkaline earth metal atom.

2. A smoking composition in accordance with claim 1 wherein the flavorant-release additive is 3-hydroxy-2,2-dimethyl-4-phenylmethylenedecanoic acid.

3. A smoking composition in accordance with claim 1 wherein the flavorant-release additive is calcium bis(3-hydroxy-2,2-dimethyl-4-phenylmethylenedecanoate).

4. A smoking composition in accordance with claim 1 wherein the flavorant-release additive is 2,2-diethyl-3-hydroxy-4-phenylmethylenedecanoic acid.

5. A smoking composition in accordance with claim 1 wherein the flavorant-release additive is calcium bis(2,2-diethyl-3-hydroxy-4-phenylmethylenedecanoate).

6. A smoking composition in accordance with claim 1 wherein the flavorant-release additive is 3-hydroxy-2-methyl-2-propyl-4-phenylmethylenedecanoic acid.

7. A smoking composition in accordance with claim 1 wherein the flavorant-release additive is calcium bis(3-hydroxy-2-methyl-2-propyl-4-phenylmethylenedecanoate).

8. A cigarette smoking product comprising (1) a combustible filler selected from natural tobacco, reconstituted tobacco and tobacco substitutes, and (2) a paper wrapper which has incorporated therein a flavorant-release additive corresponding to the formula:

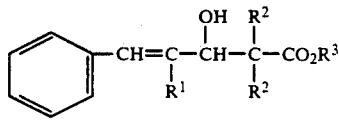

where $R^1$ is a $C_4$-$C_7$ alkyl substituent, $R^2$ is a $C_1$-$C_4$ alkyl substituent, and $R^3$ is hydrogen or an alkali metal or alkaline earth metal atom.

9. A cigarette smoking product in accordance with claim 8 wherein the paper wrapper contains between about 0.01-5 weight percent of flavorant-release additive.

10. A cigarette smoking product in accordance with claim 8 wherein the flavorant-release additive in the paper wrapper is 3-hydroxy-2,2-dimethyl-4-phenylmethylenedecanoic acid.

11. A cigarette smoking product in accordance with claim 8 wherein the flavorant-release additive in the paper wrapper is calcium bis(3-hydroxy-2,2-dimethyl-4-phenylmethylenedecanoate).

12. A cigarette smoking product in accordance with claim 8 wherein the flavorant-release additive in the paper wrapper is 2,2-diethyl-3-hydroxy-4-phenylmethylenedecanoic acid.

13. A cigarette smoking product in accordance with claim 8 wherein the flavorant-release additive in the paper wrapper is calcium bis(2,2-diethyl-3-hydroxy-4-phenylmethylenedecanoate).

14. A cigarette smoking product in accordance with claim 8 wherein the flavorant-release additive is a component of the sideseam adhesive of the paper wrapper.

15. A cigarette smoking product in accordance with claim 8 wherein the combustible filler contains between about 0.0001-5 weight percent, based on the weight of filler, of a flavorant-release additive corresponding to the formula:

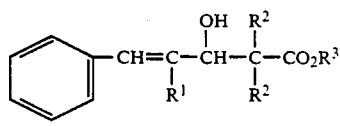

where $R^1$ is a $C_4$-$C_7$ alkyl substituent, $R^2$ is a $C_1$-$C_4$ alkyl substituent, and $R^3$ is hydrogen or an alkali metal or alkaline earth metal atom.

16. A cigarette smoking product in accordance with claim 15 wherein the flavorant-release additive in the combustible filler is 3-hydroxy-2,2-dimethyl-4-phenylmethylenedecanoic acid.

17. A cigarette smoking product in accordance with claim 15 wherein the flavorant-release additive in the combustible filler is calcium bis(3-hydroxy-2,2-dimethyl-4-phenylmethylenedecanoate).

18. A cigarette smoking product in accordance with claim 15 wherein the flavorant-release additive in the combustible filler is 2,2-diethyl-3-hydroxy-4-phenylmethylenedecanoic acid.

19. A cigarette smoking product in accordance with claim 15 wherein the flavorant-release additive in the combustible filler is calcium bis(2,2-diethyl-3-hydroxy-4-phenylmethylenedecanoate).

20. A cigarette smoking product in accordance with claim 15 wherein the flavorant-release additive in the combustible filler is 3-hydroxy-2-methyl-2-propyl-4-phenylmethylenedecanoic acid.

21. A cigarette smoking product in accordance with claim 15 wherein the flavorant-release additive in the combustible filler is calcium bis(3-hydroxy-2-methyl-2-propyl-4-phenylmethylenedecanoate).

22. $\beta$-Hydroxycarboxylic acid compounds corresponding to the formula:

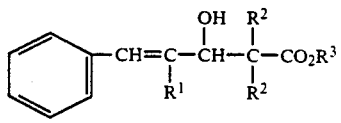

where $R^1$ is a $C_4$–$C_7$ alkyl substituent, $R^2$ is a $C_1$–$C_4$ alkyl substituent, and $R^3$ is hydrogen or an alkali metal or alkaline earth metal atom.

23. A β-hydroxycarboxylic acid compound in accordance with claim 22 wherein $R^1$ is a hexyl substituent.

24. A β-hydroxycarboxylic acid compound in accordance with claim 22 wherein $R^2$ is a methyl or ethyl substituent.

25. A β-hydroxycarboxylic acid compound in accordance with claim 22 wherein $R^3$ is hydrogen.

26. A β-hydroxycarboxylic acid compound in accordance with claim 22 wherein $R^3$ is calcium or magnesium.

27. 3-Hydroxy-2,2-dimethyl-4-phenylmethylenedecanoic acid.

28. Calcium bis(3-hydroxy-2,2-dimethyl-4-phenylmethylenedecanoate).

29. 2,2-Diethyl-3-hydroxy-4-phenylmethylenedecanoic acid.

30. Calcium bis(2,2-diethyl-3-hydroxy-4-phenylmethylenedecanoate).

31. 3-Hydroxy-2-methyl-2-propyl-4-phenylmethylenedecanoic acid.

32. Calcium bis(3-hydroxy-2-methyl-2-propyl-4-phenylmethylenedecanoate).

* * * * *